United States Patent [19]
Katz et al.

[11] Patent Number: 4,874,748
[45] Date of Patent: Oct. 17, 1989

[54] CLONING VECTORS FOR STREPTOMYCES AND USE THEREOF IN MACROLIDE ANTIBIOTIC PRODUCTION

[75] Inventors: Leonard Katz; James Tuan, both of Waukegan; James B. McAlpine, Libertyville, all of Ill.

[73] Assignee: Abbott Laboratories, North Chicago, Ill.

[21] Appl. No.: 843,116

[22] Filed: Mar. 24, 1986

[51] Int. Cl.$^4$ ................ A61K 31/71; C07H 17/08
[52] U.S. Cl. .................................. 514/29; 536/7.2; 435/253.5; 435/886
[58] Field of Search ................ 536/7.2; 514/29

[56] References Cited

U.S. PATENT DOCUMENTS

| | | | |
|---|---|---|---|
| 3,714,142 | 1/1973 | Martin et al. | 536/7.2 |
| 4,273,875 | 6/1981 | Manis | 435/253 |
| 4,331,803 | 5/1982 | Wadanabe et al. | 536/7.2 |
| 4,332,900 | 6/1982 | Manis et al. | 435/172 |
| 4,513,085 | 4/1985 | Nakatsukasa et al. | 514/253 |
| 4,740,502 | 4/1988 | Hannick et al. | 514/29 |

FOREIGN PATENT DOCUMENTS

| | | | |
|---|---|---|---|
| 2107716A | 5/1983 | United Kingdom | 435/253 |
| 2107717A | 5/1983 | United Kingdom | 435/253 |
| 2118947A | 11/1983 | United Kingdom | 435/253 |

OTHER PUBLICATIONS

Stanzak, R., et al., "Cloning and Expression in Streptomyces Lividans of Clustered Erythromycin Biosynthesis Genes from *Streptomyces Erythreus*", BIOTECHNOLOGY, 4:229–232, Mar. 1986.

Martin, Juan F., et al., "Cloning and Expression of Antibiotic Production Genes," BIOTECHNOLOGY, 2:63–72, Jan. 1984.

Bibb, Mervyn J., et al., "Cloning and Analysis of the Promotor Region of the Erythromycin Resistance Gene (ermE) of Streptomyces Erythraeus", GENE 38:215–226, (1985).

Bibb, Mervyn J., et al., "Transformation of Plasmid DNA into Streptomyces at High Frequency", NATURE, vol. 274:398–400, Jul. 27, 1978.

Bibb, Mervyn J., et al., "Physical and Genetical Characterisation of a Second Sex Factor, SCP2, for Streptomyces Coelicolor A3(2)", MOLEC. GEN. GENET. 154:155–166, (1977).

Primary Examiner—Johnnie R. Brown
Assistant Examiner—Elli Peselev
Attorney, Agent, or Firm—Roberta L. Hastreiter

[57] ABSTRACT

DNA cloning shuttle vectors, including a cosmid shuttle vector, for *E. coli* and Streptomyces are disclosed. Specifically, disclosed shuttle vectors pAL7002 (NRRL B-18055) and pNJ1 (NRRL B-18054) contain an *E. coli* origin of replication, Streptomyces replication functions, and antibiotic resistance markers for both *E. coli* and Streptomyces. In addition, pNJ1 contains a cos sequence. Novel 2-norerythromycin antibiotics A, B, C, and D, which were produced in a strain *Streptomyces erythreus* 12693-240 (NRRL B-18053) transformed by pNJ1 bearing DNA from *Streptomyces antibioticus,* are also disclosed. The present invention also provides a method for producing novel antibiotics. This method for antibiotic production is applied to the transformation of a blocked mutant of *S. erythreus* with genomic DNA from *S. antibioticus* but may be more broadly applied to genes to antibiotic-producing strains transformed into cells which are blocked in the pathway for production of a different antibiotic.

9 Claims, 4 Drawing Sheets

RESTRICTION SITE AND FUNCTIONAL MAP OF PLASMID pAL7002

RESTRICTION SITE AND FUNCTIONAL MAP OF PLASMID pNJ1

STRUCTURE OF 2-NORERYTHROMYCINS

|  | | $R_1$ | $R_2$ |
|---|---|---|---|
| 2-NORERYTHROMYCIN | A | OH | $CH_3$ |
|  | B | H | $CH_3$ |
|  | C | OH | H |
|  | D | H | H |

CARBON MAGNETIC RESONANCE SPECTRAL COMPARISONS

2-NORERYTHROMYCIN D

CLONING VECTORS FOR STREPTOMYCES AND USE THEREOF IN MACROLIDE ANTIBIOTIC PRODUCTION

BACKGROUND

The present invention relates in general to shuttle vectors for use with *E. coli* and Streptomyces and cloning of antibiotic genes using these vectors. In particular, the present invention relates to vectors pNJ1 and pAL7002 and to production of 2-norerythromycin antibiotics employing these vectors.

Cloning vectors, called *E. coli-Streptomyces* shuttle vectors, may be constructed which contain origins of replication and antibiotic resistance markers for both *E. coli* and in Streptomyces. Nakatsukasa et al., U.S. Pat. No. 4,513,085; Fayerman et al., U.K. Patent Application No. 2,107,716; Fayerman et al., U.K. Patent Application No. 2,107,717; and Hershberger et al., U.K. Patent Application No. 2,118,947. However, because Streptomyces strains are used to produce most of the clinically important antibiotics, it is desirable to obtain stable vectors which replicate and are selectable in *E. coli*, where recombinant manipulations are relatively easy to perform, and which replicate and are selectable in Streptomyces, wherein recombinantly-manipulated genes are expressed. Stability is particularly important inasmuch as some such shuttle vectors may be unstable, i.e. may be lost from their host cell along with the cloned gene they carry. See e.g. Matsushima et al., *Bio/Technology*, 4, 229-232 (1986).

Because cosmid vectors combine the opportunity to make use of the wide variety of features of plasmid vectors, including selection markers, and the large cloning capacity of phage vectors, they are particularly desirable. *E. coli-Streptomyces* cosmid shuttle vectors may be constructed to take advantage of these features. Matsushima et al., supra. Cosmid shuttle vectors which are stable with application of selection pressure are also desirable.

Erythromycin is a macrolide antibiotic product of a biosynthetic pathway in *Streptomyces erythreus* which is believed to have about thirty steps. Cosmid shuttle vectors carrying genes for antibiotic production may be used to explore biosynthesis of hybrid antibiotics. Matsushima et al., supra. Attempts to assay for the production of erythromycin may involve the use of *S. erythreus* strains having no detectable antibiotic activity which are blocked in the biosynthesis of erythromycin, such as eryA mutants which are blocked in the formation of 6-deoxyerythronolide B, an unmodified lactone. Matsushima et al., supra. Restoration of antibiotic function in such strains after transformation with a vector carrying genetic material to be tested for the production of erythromycin indicates antibiotic function is restored by the vector-borne genetic material. However, no suggestion has been made that such a technique might be employed to obtain hitherto unreported analogs of erythromycin such as norerythromycins.

SUMMARY OF THE INVENTION

A DNA cloning vector according to the present invention includes a fragment of plasmid pAL7002 having a functional *E. coli* origin of replication, functional determinants for replication in Streptomyces, a marker selectable in *E. coli*, a marker selectable in Streptomyces. More specifically, such a vector is a plasmid pAL7002 isolated from *E. coli* HB101/pAL7002 NRRL B-18055, has a molecular size of about 6.2 kb, has a thiostrepton resistance segment, has an ampicillin resistance segment, has a unique HindIII site, has a unique PstI site, has a unique PvuII site, has a unique EcoRI site, has a unique BglII site, and has two SmaI sites.

Another DNA cloning vector according to the present invention is stable under selection in *S. erythreus* and includes a fragment of plasmid pNJ1 having a functional *E. coli* origin of replication, functional determinants for replication in Streptomyces, a marker selectable in *E. coli*, a marker selectable in Streptomyces, and a cos segment. More specifically, such a vector is a plasmid pNJ1 isolated from *E. coli* HB101/pNJ1 NRRL B-18054, has a molecular size of about 8.8 kb, has a thiostrepton resistance segment, has an ampicillin resistance segment, has a unique HindIII site, has a unique PstI site, has a unique PvuII site, has a unique EcoRI site, has a unique BglII site, and has two SmaI sites.

A strain of *S. erythreus* according to the present invention has all of the identifying characteristics of *S. erythreus* 12693-240 NRRL B-18053. More specifically, a presently preferred embodiment of this strain is a biologically pure culture of *S. erythreus* producing upon cultivation in an aqueous medium containing assimilable sources of nitrogen and carbon a member from the group consisting of: 2-norerythromycin A; 2-norerythromycin B; 2norerythromycin C; and 2-norerythromycin D or pharmaceutically acceptable salts of these members.

A process for producing a 2-norerythromycin A antibiotic according to the present invention includes the step of cultivating *S. erythreus* 12693-240 NRRL B-18053 in an aqueous medium in the presence of assimilable sources of nitrogen and carbon.

A process for producing an erythromycin antibiotic according to the present invention includes the step of cultivating *S. erythreus* 12693-240 NRRL B-18053 in an aqueous medium in the presence of assimilable sources of nitrogen and carbon.

The present invention provides the hitherto unreported compound 2-norerythromycin A or a pharmaceutically acceptable salt thereof which may be obtained by means well known to those skilled in the art of obtaining pharmaceutically acceptable salts of erythromycin. This 2-norerythromycin A is preferably the 2-norerythromycin A effective in inhibiting the growth of bacteria and in substantially pure form which has a mass spectrum, FAB positive ion MH+ m/z of 720.

The present invention also provides the hitherto unreported compound 2-norerythromycin B or a pharmaceutically acceptable salt thereof which may be obtained by means well known to those skilled in the art of obtaining pharmaceutically acceptable salts of erythromycin. This 2-norerythromycin B is preferably one effective in inhibiting the growth of bacteria and one which in substantially pure form has a mass spectrum, FAB positive ion MH+ m/z of 704.

The present invention further provides the hitherto unreported compound 2-norerythromycin C or a pharmaceutically acceptable salt thereof and is preferably the 2-norerythromycin C which is effective in inhibiting the growth of bacteria and which in substantially pure form has an $^1$H-NMR spectrum comprising the partial spectrum as set forth in Table 3.

In addition, the present invention provides the hitherto unreported compound 2-norerythromycin D or a pharmaceutically acceptable salt thereof. Preferably, this 2-norerythromycin D is one which is effective in inhibiting the growth of bacteria and which in substantially pure form has an $^1$H-NMR spectrum as set forth in Table 1 and has a $^{13}$C-NMR spectrum as set forth in Table 2.

An antibiotic composition according to the present invention includes a diluent or carrier, such formulations being readily obtainable by those skilled in the art of preparing formulations for erythromycins, compatible with antibiotic activity and an antibiotic selected from the group consisting of 2-norerythromycin A, 2-norerythromycin B, 2-norerythromycin C, and 2-norerythromycin D or pharmaceutically acceptable salts of these antibiotics.

DETAILED DESCRIPTION

Figure 1:
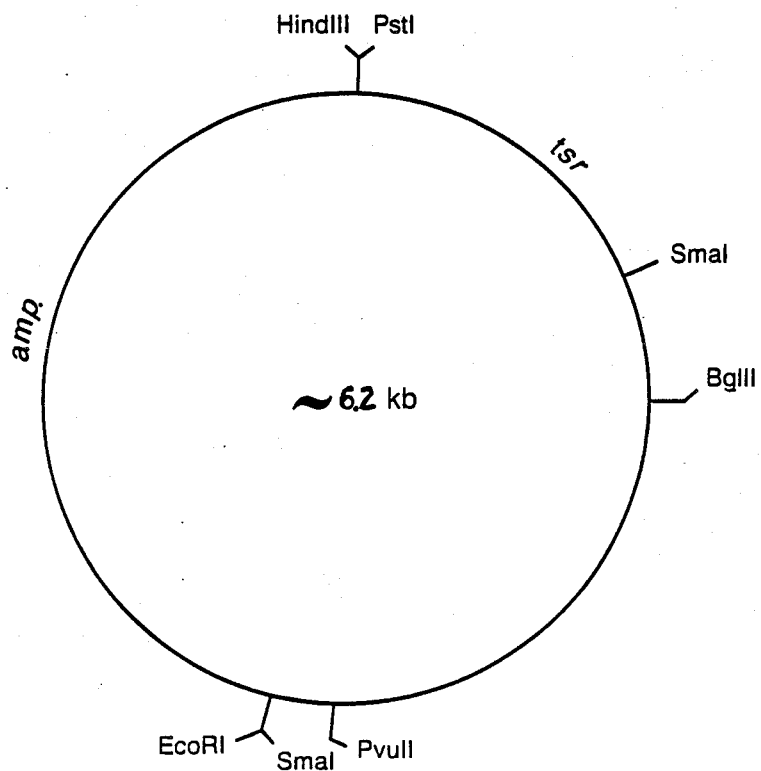
FIG. 1 is a partial restriction map of a vector pAL7002 according to the present invention.

The present invention includes selectable DNA cloning vectors comprising a fragment of plasmid pJV1 containing determinants for replication in Streptomyces, a fragment of DNA encoding selection for antibiotic resistance in Streptomyces, a functional origin of replication-containing and antibiotic resistance-conferring restriction fragment of a plasmid which is functional in E. coli and the cos sequence which contains the cohesive ends from bacteriophage lambda. Other selectable DNA cloning vectors according to the present invention include all of the above but lack the cos sequence. The vectors of this invention are functional in Streptomyces erythreus and other host strains. The vectors are useful because they are small, easily handleable, and may be introduced into a wide variety of host strains including Streptomyces erythreus and E. coli.

Because Streptomyces produce over half of the clinically important antibiotics, it is desirable to develop vectors which could be used for transfer of DNA between different species or between strains of Streptomyces in order to increase yields of existing antibiotics or in order to produce new antibiotics or their derivatives. Vectors according to the present invention are useful for these purposes. The vectors according to the present invention which contain the cos sequence are particularly useful because they may be employed to clone large DNA segments from different sources which may be up to 35 kilobases in length and which may contain twenty or more contiguous genes.

The vectors of the present invention are constructed by step-wise ligation of various DNA fragments in vitro and subsequent transformation of sensitive host cells. The fragments which contain the components of the vectors are themselves obtainable from Streptomyces or E. coli plasmids which are either commercially available or which may be obtained from commercial sources.

Reagents & Enzymes

Media for the growth of bacteria were purchased from Difco, Detroit, Mich., or Gibco, Long Island, N.Y. Restriction enzyme, calf intestinal alkaline phosphatase (CIAP) and T4 DNA ligase were purchased from Bethesda Research Laboratories, (BRL), Gaithersburg, Md., New England Biolabs, Beverley, Mass., or Boehringer Mannheim, Indianapolis, Ind. The Gigapack ™ Kit containing reagents for the in vitro packaging of bacteriophage lambda DNA was purchased from Vector Cloning Systems, San Diego, Calif. Agarose was purchased from Bio Rad, Richmond, Calif. Egg white lysozyme (3X crystallized) was obtained from Sigma, St. Louis, Mo. Thiostrepton was obtained from E. R. Squibb and Sons, Princeton, N.J.

Host Cell Cultures, DNA Sources and Vectors

E coli K12 strains JM83 and HB101 were obtained from BRL. Streptomyces lividans 66, was obtained from the John Innes Institute, Norwich, U.K. S. lividans 66 carrying plasmid pIJ704 was obtained from E. Katz at Georgetown University. Streptomyces phaeochromogenes NRRL B-3559 carrying plasmid pJV1 was obtained from the Agricultural Culture Collection (NRRL), Peoria, Ill., under the accession number NRRL B-3559.

E. coli vector pUC9 and bacteriophage lambda were purchased from Bethesda Research Laboratories or PL Laboratories, Milwaukee, Wis. Plasmid pJB8 was obtained from Mill Hill Laboratories, London, U.K. and is also available from the American Type Culture Collection, Rockville, Md., under the accession No. 37074.

General Methods

Restriction enzymes and T4 DNA ligase were used according to suppliers' instructions. Standard procedures for the growth and transformation of E. coli [Maniatis, et al., "Molecular Cloning, A Laboratory Manual," Cold Spring Harbor, N.Y. (1982)], growth and transformation of Streptomyces lividans [Bibb et al., "Developments in Streptomyces Cloning," in Experimental Manipulation of Gene Expression, Inouye ed., Academic Press, New York, N.Y., 53–87 (1983)], analysis of DNA on agarose gels [Maniatis et al., "Molecular Cloning, A Laboratory Manual," Cold Spring Harbor, N.Y. (1982)], and labeling of DNA by nick translation [Maniatis et al., "Molecular Cloning, A Laboratory Manual," Cold Spring Harbor, N.Y. (1982)]were used. Plasmids were isolated from E. coli and purified using published procedures [Maniatis et al., "Molecular Cloning, A Laboratory Manual," Cold Spring Harbor, N.Y. (1982)].

The present invention is described in more detail in the following examples.

In Example 1, the gene determining thiostrepton resistance (tsr) was subcloned from the plasmid pIJ704 into E. coli vectors such as pUC9 to yield the vector pUC9tsr. In Example 2, plasmid pJV1 is isolated from Streptomyces phaeochromogenes and a fragment of pJV1 that carries Streptomyces replication functions is subcloned into the plasmid pUC9tsr yielding the plasmid pAL7002.

Example 3 describes the subcloning of a fragment of plasmid pAL7002 (which carries Streptomyces replication functions and the tsr gene) into a fragment of plasmid pJB8 (which carries E. coli replication functions, the amp gene for selection of ampicillin resistant transformants in *E. coli* and the sequence cos which are the cohesive ends of the bacteriophage lambda) to yield the plasmid pNJ1.

In Example 5, a genomic library of *Streptomyces antibioticus* strain ATCC 11891 is constructed in pNJ1 and is introduced into *E. coli*.

In Example 6, plasmid DNA from *E. coli* carrying the genomic libraries of *Streptomyces antibioticus* ATCC 11891 is prepared and is transformed into *Streptomyces erythreus* strain 9EI41, an antibiotic non-producer, employing selection for resistance to the antibiotic thiostrepton. Thiostrepton resistant transformants are tested in Example 6 for ability to produce an antibiotic and an antibiotic producer, *S. erythreus* strain 12693-240, is detected.

Example 7 sets forth the fermentation of *S. erythreus* 12693-240, the extraction of the fermentation beer, and the identification of products. Also in Example 7, the compounds 2-norerythromycins A, B, C, and D are identified from the fermentation beer of *S. erythreus* 12693-240.

EXAMPLE 1

Construction of pUC9-tsr

The plasmid pUC9 was cut with the restriction enzyme BamHI under standard conditions and the DNA was recovered after precipitation in ethanol. This procedure renders the cut DNA free of the enzyme and buffer. The plasmid pIJ704, isolated from *Streptomyces lividans* 66 by the isolation procedure described in Example 2, was cut with the enzyme BClI and the resulting fragments were separated by agarose gel electrophoresis and were visualized under ultraviolet light after staining with ethidium bromide. A band corresponding to DNA of size approximately 1 kb was identified and removed from the gel by electroelution wherein the DNA fragments to be recovered were removed from the gel and placed in a dialysis sac containing the gel buffer. The sac was sealed and placed on a horizontal gel apparatus containing buffer and was subjected to electrophoresis for a period long enough to visualize the migration of the UV-fluorescent material from the gel slice into the surrounding buffer.

The buffer was recovered, and after purification by phenol-chloroform extraction and concentration by ethanol precipitation, approximately 2 µg of the 1 kb BClI fragment was mixed with 0.5 µg of BamHI-cut pUC9 in a standard buffer for T4 DNA ligase and 2 units of T4 DNA ligase was added in a total volume not exceeding 40 µl. The mixture was incubated at 14° C. overnight. Approximately 100 ng of the mixture was used in the transformation of competent *E. coli* JM83 cells by the procedure of Hanahan et al., *J. Mol. Biol.*, 166, 557–580 (1983) and employing selection for ampicillin resistance on LB-agar plates containing 10 µg/ml of Xgal. White colonies, the color of which indicated the presence of an insertion of DNA into pUC9, were selected, picked, and examined for their plasmid content. A strain, designated *E. coli* JM83/pUC9-tsr, carrying a plasmid of approximately 3.6 Kb which was not cut by the enzyme BamHI, was retained. The plasmid was designated pUC9-tsr. Further characterization of this plasmid revealed that it contained the restriction sites as reported for the tsr gene of pIJ704 in Thompson, et al., *Gene*, 20, 51–62 (1982).

EXAMPLE 2

Construction of Vector pAL7002

A plasmid designated pJV1, as described in Doull et al., *FEMS Microbiol. Lett.*, 16, 340–352 (1983) was isolated from mycelia of 4 to 6 day old cultures of *Streptomyces phaeochromogenes* (NRRL B-355)) using the following procedure followed throughout this application for isolating plasmids from Steptomyces. Cells were harvested by centrifugation, washed once in 10% sucrose, were resuspended in 1/50th volume of modified P medium ($MgCl_2$ and $CaCl_2$ each reduced to 0.005 M) [Okanishi et al., *J. Gen. Microbiol.*, 80, 389–400 (1974)]containing 5 mg/ml of lysozyme. The preparation was incubated at 32° C. until protoplast formation was observed. Two times the volume of lysing solution (0.3 N NaOH, 2% SDS, 0.05M EDTA) was added to the preparation. The mixture was incubated at 50° C. for 30 minutes. Two times the volume of 4 M sodium acetate, (pH 4.8) was added to the preparation and the mixture was vigorously shaken for 1 minute. The preparation was allowed to sit on ice for 30 minutes and was then centrifuged at 15,000 rpm in a refrigerated centrifuge. The supernatant was recovered and was concentrated by precipitation after addition of 1 volume of isopropanol and incubation on ice for 10 minutes. The precipitate was resuspended in TE buffer and plasmid DNA was recovered after centrifugation of the preparation in cesium chloride-ethidium bromide density gradients.

The plasmid pJV1 was cut with the enzyme SmaI and the fragments generated were subjected to agarose gel electrophoresis, phenol extraction and ethanol precipitation. Approximately 2 µg of this preparation was mixed with 0.5 µg of SmaI-cut, ethanol precipitated pUC9-tsr and ligated in the mannner described in Example 1. One-half of the preparation was then used to transform protoplasts of *Streptomyces lividans* 66 according to the procedure of Bibb et al., "Developments in Streptomyces Cloning," supra, employing selection for thiostrepton resistance. A number of these clones that appeared were examined for their plasmid content. A strain, designated *Streptomyces lividans* 66/pAL7002, that harbored a plasmid of approximately 6.2 kb was kept. The plasmid, designated pAL7002, was isolated. Plasmid pAL7002 may be isolated from *E. coli* HB101/pAL7002 which was deposited on Mar. 11, 1986 with the Agricultural Research Culture Collection (NRRL), Peoria, Ill., as deposit No. NRRL B-18055. A partial restriction and genetic map of the plasmid is shown in FIG. 1.

EXAMPLE 3

Construction of Vector pNJ1

When the ~1.05 kb BClI thiostrepton resistance-determining fragment is inserted into the BamHI site of plasmid pUC9 and the ~2.7 kb fragment of pJV1 is subsequently inserted into the SmaI site of the composite pUC9-tsr vector, the vector pAL7002 is produced. The proximity of the thiostrepton resistance determinant to the replication-functional segment in pAL7002 allows them to be subcloned into other vectors as a single HindIII-EcoRI restriction fragment of ~3.8 kb. As, for example, when the ~3.8 kb HindIII-EcoRI is subcloned into HindIII and EcoRIcut vector pJB8, the resulting vector pNJ1 is produced.

Figure 2:
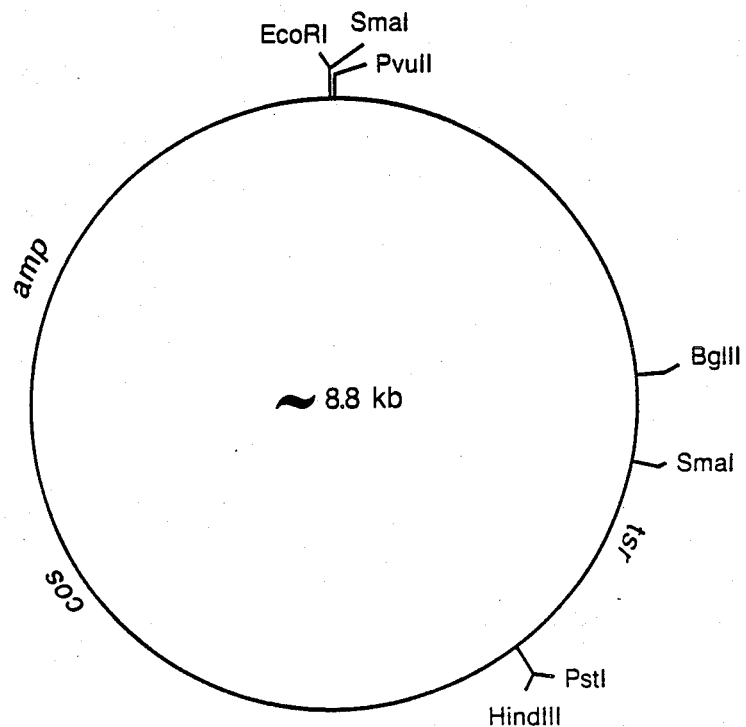
FIG. 2 is a partial restriction map of a vector pNJ1 according to the present invention.

Approximately 5 μg of pAL7002 was cut with the restriction enzyme HindIII using standard conditions. The DNA was then treated with the enzyme calf intestinal alkaline phosphatase (CIAP) to remove the terminal phosphate from the free ends of the cut plasmid. The DNA was then phenol extracted, precipitated and redissolved and then subjected to restriction with the enzyme EcoRI for 2 hours. After treatment, the DNA was phenol extracted and precipitated as described in Example 1 to form a first preparation. Similarly, 5 μg of pJB8 was first cut with the enzyme EcoRI, treated with enzyme CIAP, treated with HindIII and recovered after phenol extraction and precipitation to form a second preparation. One microgram of each preparation was mixed together and ligated as described. The resulting preparation was then transformed into competent *E. coli* HB101 cells employing selection for ampicillin resistance. Plasmid DNA was examined from a number of colonies. A strain, designated *E. coli* HB101/pNJ1, carrying a plasmid of approximately 8.8 kb was kept. The plasmid was designated pNJ1. Plasmid pNJ1 may be isolated from *E. coli* HB101/pNJ1 which was deposited on Mar. 11, 1986, with the Agricultural Research Culture Collection (NRRL), Peoria, Ill., under the accession No. B-18054. A partial restriction map of the plasmid is shown in FIG. 2.

EXAMPLE 4

Construction of *S. erythreus*/pAL7002 and *S. erythreus*/pJN1

Plasmids pAL7002 or pNJ1 were transformed into protoplasts of *Streptomyces erythreus* according to the following procedure.

In a general procedure for growth of Streptomyces and conversion to protoplasts, spores, or vegetative mycelia of *Streptomyces erythreus* were inoculated into 50 ml of SGGP medium (0.4% Tryptone, 0.4% yeast extract, 0.05% MgSO$_4$, 1% glucose. 0.2% glycine, 0.01 M potassium phosphate buffer, pH7.0) and were incubated at 28° C. with shaking at 200 rpm for a period of 4 to 6 days. The cells were then harvested by centrifugation, were washed once in P medium [Okanishi et al., supra,]and were resuspended in P medium containing lysozyme at a final concentration of 5 mg/ml. The suspension was incubated at 32° C. for time sufficient (generally 15 to 60 min) to allow protoplast formation as monitored by examination of samples under a microscope. Protoplasts were collected by low speed centrifugation, washed free of the lysozyme in P medium and were resuspended at a final density of >10$^{10}$/ml. Protoplasts were either used directly for transformation or were stored at −70° C. after addition of DMSO to a final concentration of 4%.

In the transformation of *S. erythreus* protoplasts, 0.5-5 μg of DNA in TE buffer [Maniatis et al., "Molecular Cloning, A Laboratory Manual," Cold Spring Harbor, N.Y., (1982)]was mixed with 10 μg of heparin, was chilled on ice for 20 minutes and then was brought to room temperature where all subsequent steps take place. Protoplasts at a concentration of about 10$^9$/ml were added to the DNA followed after 1 minute by addition of 25% polyethylene glycol 3350 in PT medium (10.3% sucrose, 0.025% K$_2$SO$_4$, 0.025M TES buffer, pH 7.2, 0.025 M each of CaCl$_2$ and MgCl$_2$ and trace elements as described in Bibb et al., *Nature*, 274, 398-400 (1978)). After 2 minutes standing, undiluted aliquots were spread with the aid of a plastic rod over the surface of predried R3M agar media [2.2% agar, 0.4% each of Tryptone, Casamino acids and Yeast Extract, 0.025M Tris-HCl, pH 7.2, 0.05% KH$_2$PO$_4$, 0.05M each of CaCl$_2$ and MgCl$_2$, 0.0025M NaOH, 0.025% K$_2$SO$_4$, 1% glucose, 10.3% sucrose, and trace elements as in Bibb et al., *Nature*, 274, 398–400 (1978)]. Plates were incubated at 28° C. for 18 to 36 hours until regeneration was evident. For selection of thiostrepton resistant (Thio®)transformants, the plates were overlayed with 5 ml of semisolid Trypticase Soy Broth containing 0.6% agar and 40 μg/ml of thiostrepton, and were incubated at 32° C. until colonies appeared. The ability of colonies to grow on a medium containing thiostrepton indicated that they were composed of transformants containing the Thio® segment.

EXAMPLE 5

Construction of a Genomic Library of *Streptomyces antibioticus* ATCC 11891 in pNJ1 and Introduction into *E. coli*

Genomic DNA from *S. antibioticus* strain, available from the American type Culture Collection as No. ATCC 11891 was prepared from protoplasts of *Streptomyces antibiotics*, prepared as described in Example 4, which were lysed with a solution of SDS or sarkosyl. The lysate is then deproteinated by repeated treatments with phenol-chloroform, followed by concentration by ethanol precipitation. The dissolved precipitated is treated with ribonuclease, then re-extracted with phenol-chloroform. After precipitation with ethanol, the dissolved material is usable for cloning. The dissolved material was partially cut with the enzyme Sau3Al to yield fragments ranging in size from ~1 kb to >40 kb.

The DNA fragments were treated with the enzyme CIAP, were extracted with phenol, and were precipitated with ethanol (preparation A). Plasmid pNJ1 was digested with EcoRI, was phenol extracted, was treated with CIAP, was phenol extracted again, was treated with the restriction enzyme BglII, was phenol extracted and was precipitated (preparation B). Similarly, a second sample of pNJ1 was digested with the restriction enzyme HindIII, was treated with CIAP, and then was digested with BglII (preparation C). A mixture consisting of 0.5μg of preparation B, 0.5 μg of preparation C and 5 μg of preparation A was prepared in ligation buffer and was treated with T4 DNA Ligase at 14° C. overnight. The material was then subjected to in vitro packaging in bacteriophage lambda using the Gigapack ™ kit employing the protocols obtained from the supplier.

After packaging was completed, the preparation was mixed with *E. coli* HB101 cells in 0.01 M MgSO$_4$ to permit adsorption of the phage onto the cells and allowed to stand at room temperature for 20 minutes. The cells were then transferred to L Broth and allowed to grow for a period of 1 hour before addition of ampicillin to the medium to a final concentration of 50 μg/ml. The culture was incubated overnight and plasmid DNA was extracted from the preparation.

EXAMPLE 6

Construction of *Streptomyces erythreus* 12693-240

The mixed plasmid preparation of pNJ1 carrying components of the genomic library of *Streptomyces antibioticus* ATCC 11891, an oleandomycin-producing strain, prepared as described in Example 5, was isolated from *E. coli* and transformed into protoplasts of *Strepto*-

*myces erythreus* strain 9EI41, an eryA strain, employing selection for thiostrepton resistance as described in Example 4. Individual transformants that arose were tested for the production of one or more substances which either killed or inhibited the growth of a thiostrepton resistant culture of *Staphylococcus aureus* in an agar plug test as follows. Transformants, obtained by picking isolates which grew in the presence of thiostrepton, were grown on SLM-3 agar medium (1% cornstarch, 0.5% cornsteep liquor, 0.00012% $FeSo_4$, 0.3% $CaCO_3$, 1.5% agar, pH adjusted to 7.0) containing thiostrepton at 2–5 μg/ml to maintain selection for the presence of vectors containing the gene for resistance to thiostrepton, for 7–10 days at 32° C. A small plug of the agar, taken from the area of dense growth was then placed on the surface of an agar medium seeded with a suspension of thiostrepton resistant *Staphylococcus aureus* cells. The medium was incubated overnight at 37° C. If an antibiotic was produced by the Streptomyces culture, a zone of inhibition of the *S. aureus* was seen to surround the agar plug.

One isolate, designated *Streptomyces erythreus* 12693-240, exhibited the characteristic of, when grown in the presence of thiostrepton, producing one or more substances that killed or inhibited the growth of thiostrepton-resistant *Staphylococcus aureus* cells. *S. erythreus* 12693-240 was deposited on Mar. 11, 1986, and made part of the permanent culture collection of the Agricultural Research Culture Collection (NRRL) Peoria, Ill., under the accession number NRRL B-18053.

EXAMPLE 7

Antibiotics from *S. erythreus* 12693-240

Streptomyces cells of strain 12693-240 were inoculated into 500 ml of SCM medium (1.5% soluble starch, thiostrepton at 2 μg/ml and grown for 3 to 6 days at 32° C. thiostrepton at 2 μg/ml and grown for 3 to 6 days at 32° C. The entire culture was then inoculated into 10 liters of fresh SCM medium containing thiostrepton at 2 μg/ml and 5% soy bean oil in a fermenter. The fermenter was operated for a period of 7 days at 32° C. maintaining constant aeration and pH at 7.0.

At harvest, the fermentation beer was adjusted to pH 9.2 with 5N KOH, centrifuged and the supernatant beer was extracted sequentially with two half-volumes of ethyl acetate. The combined ethyl acetate extracts were extracted with two half-volumes of pH 4.8, 2% citric acid-sodium citrate aqueous buffer. The combined aqueous layers were adjusted to pH 9.2 with 5 N KOH and extracted with 2 halfvolumes of ethyl acetate. The combined ethyl acetate extracts were concentrated to yield a crude concentrate of lipophilic extractables. The crude concentrate was purified by chromatography over lipophilic gel exclusion resins such as Sephadex LH-20 ®(Pharmacia, Piscataway, N.J.) in a solvent such as methanol, or in mixed solvents such as chloroform hexane 1:1. Antibiotic-containing fractions may be detected by bioassay on pH 8 agar media seeded with a macrolide sensitive strain of *Staphylococcus aureus*.

Separation of antibiotic congeners of similar structure may be achieved by countercurrent chromatography using an Ito Coil Planet Centrifuge ®, (P.C., Inc., Potomac, Md.,) with a suitable two-phase system. Multiple chromatographic separations may be required to separate all of the bioactive congeners from a single fermentation.

A 10 liter fermentation of the strain 12693-240 yielded an oil (264 mg) as the crude extractable basic fraction. This was subjected to counter current chromatography on an Ito Coil Planet Centrifuge using a 2-phase system (n-heptane, benzene, isopropanol, acetone, 0.05 M; pH7.0 potassium phosphate buffer in the ratio 5:10:3:2:5, respectively, with the lower phase as the stationary phase). A flow rate of approximately 4 ml/min and a coil spin rate of approximately 800 r.p.m. was maintained. The sample was injected onto the column in 10 ml of upper phase using a Rheodyne TM injection loop. Approximately 8 ml fractions were collected. Each fraction was bioassayed against *Staphlococcus aureus* 6538P using 20 μl discs in disc diffusion assay on Streptomycin assay agar plates (Difco) adjusted to pH 8 prior to autoclaving. Fractions were combined, on the basis of bioactivity profile, in three bioactive pools. From each of these the solvent was removed and the resulting residue was partitioned between chloroform and dilute aqueous ammonium hydroxide. The chloroform layer was removed, was washed with water, and then was concentrated to a residue. These were examined in $CDCl_3$ by $^1H$-NMR spectroscopy.

Antibiotics were characterized spectroscopically using high yield FT NMR spectroscopy. A variety of one dimensional and two dimensional pulse techniques were employed with both homo and heteronuclear observations of $^1H$ and $^{13}C$ nuclei. These data were supplemented by high resolution mass spectrometry using both fast-atom bombardment and electron impact sources.

A first activity band eluted from the chromatogram was shown to be a mixture of closely related macrolides and was rechromatographed.

A second activity band was shown to be 2-norerythromycin D (FIG. 5). It was characterized by extensive $^1H$-NMR decoupling experiments and CMR spectrum as respectively illustrated in Tables 1 and 2. In the absence of published spectra for erythromycin D the comparative data for Erythromycins A and B in Table 2 is as published in Terui et al., *Tetrahedron Lett.*, 1975, 2583-2586 (1975) except that the assignments for 2CH₃ and 8CH³ are interchanged (as was suggested as a possibly proper assignment in Terui et al., supra). Data for erythromycin C were generated at Abbott Laboratories.

In Table 1, TMS is an abbreviation for tetramethylsilane, s is an abbreviation for singlet, d is an abbreviation for doublet, t is an abbreviation for triplet, q is an abbreviation for quartet, and m is an abbreviation for multiplet.

TABLE 1

| $^1H$—NMR SPECTRUM OF 2-NORERYTHROMYCIN D | | |
|---|---|---|
| Assigment | Chemical Shift (ppm from TMS) | Splitting pattern | Coupling Constants(Hz) |
| H-13 | 5.44 | d of d of d | 1.8, 4.2, 9.6 |
| H-1" | 4.99 | d (broad) | 4.0, <1.0 |
| H-1' | 4.32 | d | 7.0 |
| H-3 | 4.24 | d of t | 11.4, 2.5 |
| H-5" | 3.84 | d of q | 9.6, 5.9 |
| H-11 | 3.75 | d (broad) | 10.0, <1.0 |
| H-5' | 3.58 | d of d of q | 10.7, 1.9, 6.2 |
| H-5 | 3.55 | d | 7.0 |
| H-2' | 3.25 | d of d | 7.0, 10.3 |
| OH | 3.19 | s (broad) | |
| H-10 | 3.01 | q (broad) | 7.0, <1.0 |
| H-4" | 3.00 | d | 9.6 |
| H-8, H3' | 2.67 | m | |
| H-2a | 2.66 | d of d | 12.1, 11.4 |
| H-2e | 2.50 | d of d | 3.0, 12.1 |
| $(CH_3)_2N$ | 2.37 | s | |
| H-4 | 2.26 | q of d of d | 7.0, 7.7, 12.2 |

TABLE 1-continued
$^1$H—NMR SPECTRUM OF 2-NORERYTHROMYCIN D

| Assignment | Chemical Shift (ppm from TMS) | Splitting pattern | Coupling Constants(Hz) |
|---|---|---|---|
| H-7a | 2.02 | d of d | 12.1, ~15 |
| H-2″e | 2.01 | d of d | 14.3, <1.0 |
| H-2″a | 1.88 | d of d | 14.3, 4.0 |
| H-4′e | 1.76 | d of d of d | ~13, 1.5, 1.9 |
| H-14a | 1.71 | q of d of d | 1.8, 7.0, ~13 |
| H-12 | 1.65 | m | |
| H-7e | 1.64 | d of d | ~15, 2 |
| H-14b | 1.48 | q of d of d | 4.2, 7.0, ~13 |
| $CH_3$—$C_6$ | 1.46 | s | |
| $CH_3$—6″ | 1.33 | d | 5.9 |
| H-4′a | ~1.30 | m | |
| $CH_3$—$C_3″$ | 1.26 | s | |
| $CH_3$—6′ | 1.24 | d | 6.3 |
| $CH_3$—$C_8$ | 1.16 | d | 7.0 |
| $CH_3$—$C_4$ | 1.12 | d | 7.7 |
| $CH_3$—$C_{10}$ | 1.00 | d | 7.0 |
| $CH_3$—15 | 0.89 | t | 7.3 |
| $CH_3$—$C_{12}$ | 0.87 | d | 7.0 |

TABLE 2
$^{13}$C—NMR SPECTRUM OF 2-NORERYTHROMYCIN D AND COMPARISON WITH VARIOUS ERYTHROMYCINS

| Assignment | Erythromycin A | Erythromycin B | Erythromycin C | 2-Norerythromycin D |
|---|---|---|---|---|
| C-1 | 175.5 | 175.8 | 175.5 | 170.6 |
| 2 | 44.8 | 44.7 | 45.0 | 37.6 |
| 3 | 80.0 | 80.2 | 83.2 | 78.6 |
| 4 | 39.4 | 39.5 | 39.4 | 37.4 |
| 5 | 83.6 | 83.5 | 85.0 | 84.0 |
| 6 | 74.8 | 74.8 | 75.2 | 75.3 |
| 7 | 38.1 | 38.1 | 38.6 | 38.1 |
| 8 | 45.8 | 44.7 | 45.0 | 45.5 |
| 9 | 221.1 | 219.1 | 22.0 | 220.9 |
| 10 | 38.2 | 39.0 | 37.8 | 38.2 |
| 11 | 68.7 | 69.3 | 69.5 | 69.5 |
| 12 | 74.8 | 39.8 | 74.6 | 39.7 |
| 13 | 77.0 | 75.2 | 77.3 | 75.3 |
| 14 | 21.3 | 25.6 | 21.3 | 25.6 |
| 2$CH_3$ | 16.2 | 15.5 | 16.2 | |
| 4$CH_3$ | 9.1 | 9.2 | 9.2 | 8.5 |
| 6$CH_3$ | 26.8 | 27.3 | 26.9 | 27.2 |
| 8$CH_3$ | 18.5 | 18.5 | 18.4 | 18.0 |
| 10$CH_3$ | 12.0 | 9.2 | 11.9 | 9.0 |
| 12$CH_3$ | 16.0 | 9.2 | 16.0 | 9.5 |
| 14$CH_3$ | 10.5 | 10.3 | 10.6 | 10.4 |
| 1′ | 103.1 | 103.0 | 104.8 | 103.6 |
| 2′ | 70.9 | 70.9 | 70.8 | 70.6 |
| 3′ | 65.3 | 65.5 | 65.5 | 65.5 |
| 4′ | 28.7 | 28.7 | 28.4 | 28.9 |
| 5′ | 68.8 | 68.8 | 68.8 | 69.2 |
| 6′ | 21.3 | 21.3 | 21.0 | 21.3 |
| N($CH_3$)$_2$ | 40.3 | 40.2 | 40.2 | 40.2 |
| 1″ | 96.2 | 96.5 | 98.7 | 94.9 |
| 2″ | 35.0 | 35.0 | 40.4 | 41.4 |
| 3″ | 72.5 | 72.5 | 69.4 | 69.7 |
| 4″ | 77.9 | 77.9 | 76.4 | 76.4 |
| 5″ | 65.4 | 65.6 | 66.1 | 66.6 |
| 6″ | 18.3 | 18.5 | 18.3 | 18.4 |
| 3″$CH_3$ | 21.3 | 21.3 | 25.5 | 25.7 |
| $OCH_3$ | 49.4 | 49.4 | | |

In Table 1, the splitting pattern of a doublet of a triplet for H-3 indicates that H-3 is coupled to three other protons which have to be protons on C-2 or C-4, so that a methyl group must be missing from the material in the second activity band. The splitting pattern for H-5 is a sharp doublet indicating that no extra proton is present on C-4. Furthermore, as shown in Table 2, the absence of methyl substitution at C-2 is consistent with the change in the $^{13}$C spectrum of the position of the peak from the position it occupies for erythromycins A, B, and C.

Figure 3:
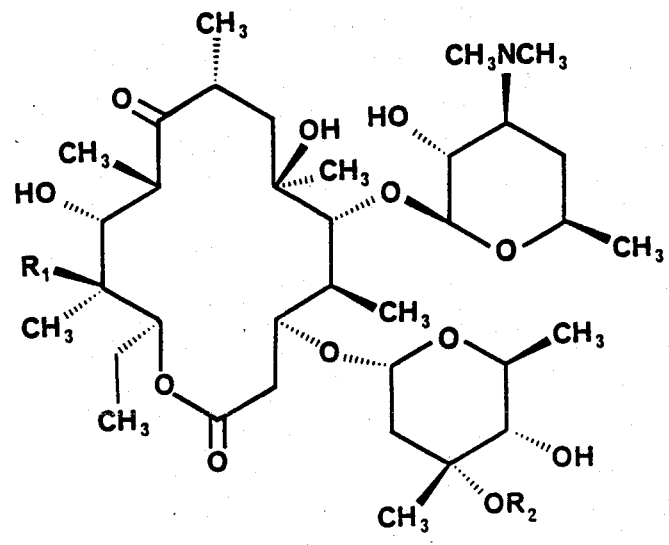
FIG. 3 is a composite diagrammatic representation of the structure of 2-norerythromycins A, B, C, and D.

The third activity band was shown to be 2-norerythromycin C, illustrated in FIG. 3, by an $^1$H-NMR spectrum, as indicated in Table 3, and by high resolution mass spectrum. The third activity band exhibited an FAB positive ion MH+ m/z of 706.

In Table 3, TMS is an abbreviation for tetramethylsilane, s is an abbreviation for singlet, d is an abbreviation for doublet, t is an abbreviation for triplet, q is an abbreviation for quartet, and m is an abbreviation for multiplet.

TABLE 3
PARTIAL $^1$H—NMR SPECTRUM OF 2-NORERYTHROMYCIN C

| Assignment | Chemical Shift (ppm from TMS) | Splitting Pattern | Approximate Coupling Constants (Hz) |
|---|---|---|---|
| H-13 | 5.10 | d of d | 2.7, 11 |
| H-1″ | 5.0 | d (broad) | 3, <1 |
| H-1′ | 4.28 | d | 7 |
| H-3 | 4.22 | d of t | 9.6, ~2 |
| H-5″ | 3.8 | m | |
| H-11 | 3.75 | s (broad) | |
| H-5 | 3.54 | d | 7.2 |
| H-5 | 3.53 | m | |
| H-2 | 3.21 | d of d | 7.0, 10.5 |
| H-10 | 3.1 | q broad | 7.2 |
| H-4″ | 3.0 | d | 9.3 |
| H-2a | 2.68 | t | 11.8 |
| H-8 | 2.65 | m | |
| H-3 | 2.60 | m | |
| H-2e | 2.46 | d of d | 2.6, 11.8 |
| ($CH_3$)$_2$N | 2.3 | s | |
| H-4 | 2.13 | broad quintet | 7.2 |
| $CH_3$—6 | 1.48 | s | |
| $CH_3$—6″ | 1.33 | d | 6.0 |
| $CH_3$—$C_{12}$, | 1.26 | s | |
| $CH_3$—$C_3″$ | | | |
| $CH_3$—15 | 0.85 | t | 7.2 |

In Table 3, the position of the splitting pattern of the signal at 4.22, readily assignable to H-3, is indicative in this molecule that a methyl group is missing from the C-2 position. The coupling pattern of proton signal of a doublet of doublets at 5.10 assigned to the H-13 proton is indicative of hydroxylation of C-12 of the macrolide structure as in erythromycins A and C. This, in conjunction with the mass spectral data, supports assignment of the third activity band as 2-norerythromycin C.

The first activity band was rechromatographed on an Ito Coil Planet Centrifuge ® using as the two-phase system carbon tetrachloride, choloroform, methanol, 0.01 M pH 5 aqueous sodium acetate-acetic acid buffer in the ratio 1:1:1:1 with the lower phase as the stationary phase. The flow rate was approximately 4 ml/min., the coil spin rate of 800 r.p.m. and the injection volume 2 ml. Three activity bands were eluted. A first activity band eluted from the column was identified by $^1$H-NMR as 2-norerythromycin A as $^1$illustrated in FIG. 3. Mass spectrum, FAB positive ion MH+ m/z was 720.

The second activity band was identified by $^1$H-NMR spectrum as erythromycin A (identical to the spectrum of an authentic sample).

The third activity band was identified as 2-norerythromycin B as illustrated in FIG. 5 by $^1$H-NMR spectrum and by mass spectrum FAB positive ion MH+ m/z of 704.

Mass spectra were run in the fast atom bombardment (FAB) positive ion mode on the first and third activity bands of the rechromatographed material, as noted above. The peaks attributable to the protonated molecular ion (MH+) species observed at m/z 720 and m/z 704 were respectively consistent with mass/charge (m/z) ratios expected for 2-norerythromycin A and 2-norerythromycin B. In each case, a major degradation ion peak attributable to the protonated basic fraction resulting from loss of a neutral sugar from the corresponding parent was observed. This peak was at m/z 562 for 2-norerythromycin A and m/z 546 for 2norerythromycin B. These mass spectral peaks and their association with bioactive bands co-produced with well-characterized 2-norerythromycins C and D provide strong circumstantial evidence for an identification of the bioactive components as being 2-norerythromycin A and 2norerythromycin B.

Figure 4:
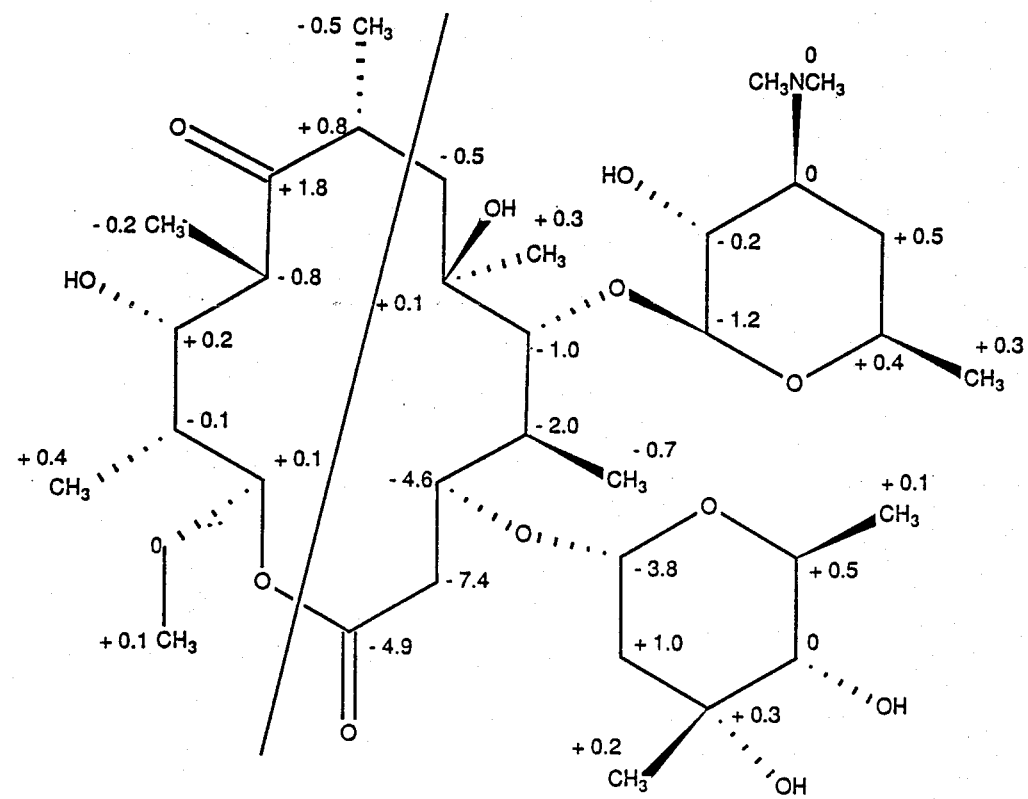
FIG. 4 is a diagrammatic representation of the association between differences in the $^{13}$C NMR spectra of erythromycin B or C and 2-norerythromycin D and the structures thereof.

It is well known that erythromycin A in its pharmaceutically useful form is subject to acidic degradation to 8,9-anhydroerythromycin A-6,9-hemiketal and to erythromycin A-6,9,12 spiroketal. Both of these products are essentially devoid of antibacterial activity. Intermediates in the formation of these inactive products are the various possible epimeric hemiketals involving the 6 or 12 hydroxyl groups and the 9-ketone function. These four possible hemiketals are normally in tautomeric equilibrium with the dihydroxy ketone form. It is interesting that an examination of chemical shift differences between the carbons of 2-norerythromycin D and appropriate carbons from available reference spectra of erythromycin B and erythromycin C, as provided in FIG. 4, shows three specific areas of major difference. In FIG. 4, differences between spectral values for 2-norerythromycin D and the indicated erythromycin reference are given adjacent the position in the erythromycin structure to which they correspond. The largest differences occur in the region of C-2, as would be expected for change or substitution at that position. Major differences also occur in the vicinity of the anomeric carbons of the sugars. This probably reflects a lesser degree of conformational rigidity for these sugars in the 2-nor compound as compared to the parent antibiotics. The other postion of major difference is in the vicinity of C-9 and this most probably reflects differences in the relative tautomeric populations of the hemiketal forms of 2-nor compounds as compared to those for the 2-methyl parents. This difference will almost certainly result in differences in rates of conversion to the 8,9 anhydro-6,9 hemiketal and the 6,9,12 spiroketal derivatives (where applicable) between 2-norerythromycins and currently available erythromycins, and, hence, an increase in the stability of the 2-norerythromycins over the currently available erythromycin antibiotics.

In addition, the quantity of material assayed with the size of zones surrounding discs in the disc assay described above indicate that 2-norerythromycin A and 2norerythromycin B are potent antibiotics, at least comparable in potency to the corresponding erythromycin A and B. Similarly, although 2-norerythromycin C and 2norerythromycin D are suggested to be relatively weaker antibiotics than 2-norerythromycins A and B, this relative potency is consistent with the relative potency of the corresponding erythromycins C and D which are relatively weaker antibiotics than are erythromycins A and B.

Although the present invention has been described in terms of a preferred embodiment, it is understood that variations and modifications will occur to those skilled in the art. For example, although plasmids pAL7002 and pNJ1 employ a ~2.7 kb SmaI restriction fragment of pJV1 as a functional replication segment in Steptomyces, other segments of pJV1 may be used, including a ~4.6 kb BamHI fragment of a ~4.7 kb KpnI fragment. These fragments are ligated to a segment of DNA containing the genetic determinant for thiostrepton resistance in Streptomyces. In addition although in the present invention, the segment of DNA determining thiostrepton resistance described herein was a ~1.05 Kb BClI fragment, obtained from the plasmid pIJ704, other fragments containing the thiostrepton resistance gene may also be employed, including all or part of plasmids pIJ350, pI702, pI703, pI704, pI705, or pIJ61 as examples, all of which may be obtained from the collection at the John Innes Institute, Norwich, U.K.. Plasmid pIJ702, available from the American Type Culture Collection, Rockville, Md., under the accession number 35287, may be directly substituted in the procedures employing pIJ704 herein. Alternatively, the thiostrepton resistance gene may be isolated from the original source, the genome of the strain *Streptomyces azureus* and ligated to the functional replication segment of pNJ1 or pAL7002.

Likewise, although DNA segments conferring resistance to thiostrepton was exemplified herein, other DNA segments which confer resistance to the same or different antibiotics, including erythromycin, streptomycin, chloramphenicol, hygromycin, neomycin, tylosin, picromycin and the like can be used by those skilled in the art either as replacements of, or in addition to the drug resistance segments described here, by ligation to the replication-determining segments of pAL7002 or pNJ1 to result in functional cloning vectors that are within the scope of the present invention.

While various restriction fragments were ligated together to form plasmids pAL7002 and the other vectors of the present invention, those skilled in the art understand that it is possible to modify the fragments to facilitate ligation by either attaching DNA oligonucleotide linkers to the fragments or by creating blunt ends on the fragments by a variety of techniques to allow non-homologous ends to be ligated together or to permit the construction of novel restriction sites of pAL7002 or its derivatives or the other vectors present in the invention to facilitate subsequent cloning experiments. Furthermore, while the vectors of the present invention represent the products of ligation of various restriction fragments to yield a given DNA sequence evidenced by the restriction maps shown for the present invention, those skilled in the art understand that ligation of two fragments with homologous restriction-cut ends will yield products with two possible orientations but which share all the properties of the vectors described for the present invention. The present invention, therefore, includes within its scope, all functional vectors constructed from the same restriction fragments as those described here but which are arranged within the vector in any of all possible orientations.

The cloning vectors present in this invention are not limited for use in a single species or strain of Streptomyces but are applicable to a wide variety of species and strains, especially those which produce antibiotics or other compounds which may be converted into antibiotics by chemical on biological means. Such species or strains which produce antibiotics of the macrolide type include, but are not limited to *S. erythreus, S. antibioticus, S. venezuelae, S. fradiae,* and *S. narbonensis*, as examples. Such species or strains which produce antibiotics of the aminoglycoside type include, but are not limited to *S. kanamyceticus, S. tennebrarius, S. hygroscopicus, S. kasugaensis,* and *S. bikiniensis,* as examples. Such strains or species which produce antibiotics of the β-lactam type include, but are not limited to *S. clavuligerus, S. lactamdurans, S. viridochromogenese, S. rochei,* and *S. flavus,* as examples. Such strains or species which produce antibiotics of the polyether type include but are not limited to *S. albus, S. griseus, S. aureofasciens, S. ribosidificus,* and *S. violaceoniger,* as examples. Such specie or strains which produce antibiotics of the glycopeptide type include, but are not limited to *S. orientalis* and *S. candidus,* as example. The vectors of the present invention are also particularly useful in other hosts of Streptomyces including, but not limited to *S. lividans* 66, *S. coelicolor,* and *S. parvulus,* as examples, which do not fall into the categories listed above.

Although methods for the transformation of protoplasts of *S. lividans* and *S. erythreus* are described in the present invention, those skilled in the art understand the methodology employed for the generation of protoplasts of Streptomyces and transformation of said protoplasts with the vectors of the present invention, including the use of regeneration medium and selection for antibiotic resistance carried on the vectors may be applied to transformation of other strains.

Accordingly, it is intended that all such equivalent modification and variations should come within the scope of the invention as claimed.

We claim:

1. The compound 2-norerythromycin A, which is a compound of the formula:

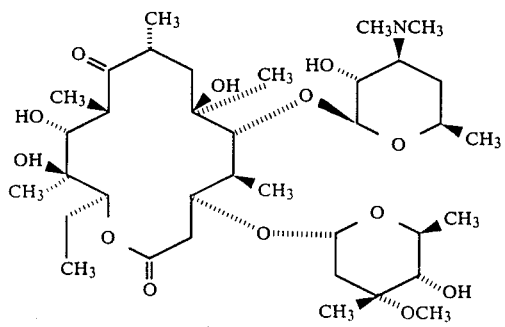

or a pharmaceutically acceptable salt thereof.

2. 2-norerythromycin A as recited in claim 1 wherein said 2norerythromycin A in substantially pure form has a mass spectrum, FAB ion MH+ m/z of 720.

3. The compound 2-norerythromycin B, which is a compound of the formula:

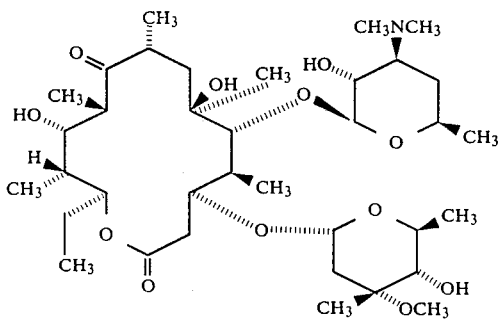

4. 2-norerythromycin B as recited in claim 3 wherein said 2-norerythromycin B in substantially pure form has a mass spectrum, FAB positive ion MH+ m/z of 704.

5. The compound 2-norerythromycin C, which is a compound of the formula:

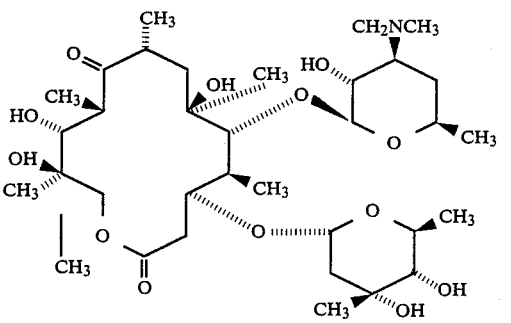

or a pharmaceutically acceptable salt thereof.

6. 2-norerythromycin C as recited in claim 5 wherein said 2-norerythromycin C in substantially pure form has an FAB positive ion MH+ m/z of 706 and has an $^1$H-NMR spectrum comprising the partial spectrum as set forth in Table 3.

7. The compound 2-norerythromycin D, which is a compound of the formula:

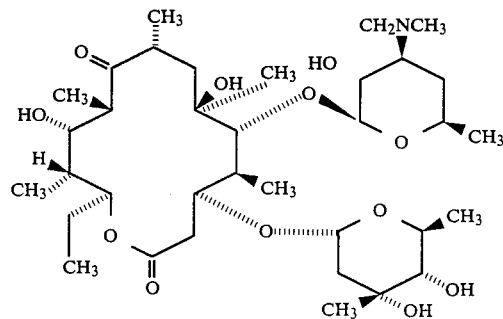

or a pharmaceutically acceptable salt thereof.

8. 2-norerythromycin D as recited in claim 7 wherein said 2-norerythromycin D in substantially pure form has an $^1$H-NMR spectrum as set forth in Table 1 and has a $^{13}$C-NMR spectrum as set forth in Table 2.

9. An antibiotic composition comprising:
   a diluent or carrier compatible with antibiotic activity; and
   an effective amount of an antibiotic selected from the group consisting of:
   2-norerythromycin A:

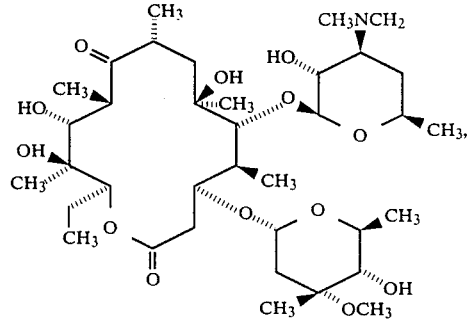

or a pharmaceutically acceptable salt thereof;
2-norerythromycin B:
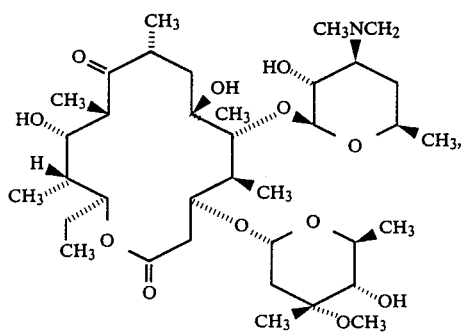
or a pharmaceutically acceptable salt thereof;
2-norerythromycin C:
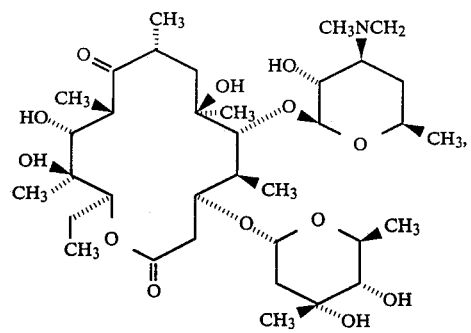
or a pharmaceutically acceptable salt thereof; and
2-norerythromycin D:
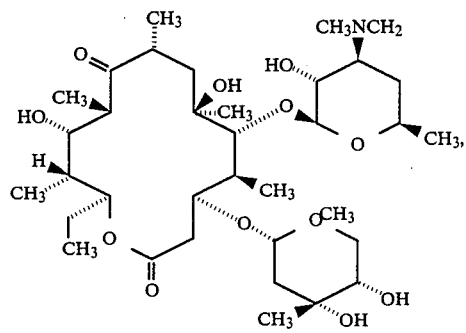
or a pharmaceutically acceptable salt thereof.
* * * * *

UNITED STATES PATENT AND TRADEMARK OFFICE
CERTIFICATE OF CORRECTION

PATENT NO. : 4,874,748

DATED : October 17, 1989

INVENTOR(S) : L. Katz, et al.

Page 1 of 4

It is certified that error appears in the above-identified patent and that said Letters Patent is hereby corrected as shown below:

Title Page, "Other Publications" Section:
  Line 2, change "Lividans" to --lividans--:
  Line 3, change "Erythreus" to --erythreus--;
  Line 10, change "(ermE)" to --(ermE)--, change "Erythraeus" to --erythraeus-- and italicize "Streptomyces erythraeus";
  Line 13, "Streptomyces" needs to be italicized.
  Lines 16-17, change "Coelicolor" to --coelicolor-- and italicize "Streptomyces coelicolor".
Column 1, Line 8, "Streptomyces" needs to be italicized.
Column 1, Line 16, "Streptomyces" needs to be italicized.
Column 1, Line 20, "Streptomyces" needs to be italicized.
Column 1, Line 65, "Streptomyces" needs to be italicized.
Column 1, Line 66, "Streptomyces" needs to be italicized.
Column 2, Line 3, change "HindIII" to --HindIII--.
Column 2, Line 4, change "PstI" to --PstI--, change "PvuII" to --PvuII--, and change "EcoRI" to --EcoRI--.
Column 2, Line 5, change "BglII" to --BglII and change SmaI to --SmaI--.
Column 2, Line 10, "Streptomyces" needs to be italicized.
Column 2, Line 11, "Streptomyces" needs to be italicized.
Column 2, Line 16, change "HindIII" to --HindIII and change "PstI" to --PstI--.
Column 2, Line 17, change "PvuII" to -- PvuII-- and change "EcoRI" to --EcoRI--.
Column 2, Line 18, change "BglII" to --BglII-- and change "SmaI" to --SmaI--.
Column 3, Lines 33-34, "Streptomyces" needs to be italicized.
Column 3, Line 35, "Streptomyces" needs to bew italicized.
Column 3, Line 38, change "cos" to --cos--.
Column 3, Line 47, "Streptomyces" needs to be italicized.

UNITED STATES PATENT AND TRADEMARK OFFICE
CERTIFICATE OF CORRECTION

PATENT NO. : 4,874,748

DATED : October 17, 1989

INVENTOR(S) : L. Katz, et al.

It is certified that error appears in the above-identified patent and that said Letters Patent is hereby corrected as shown below:

Column 3, Line 65, "Streptomyces" needs to be italicized.
Column 4, Line 19, change "E coli" to --E. coli--.
Column 4, Line 61, "Streptomyces" needs to be italicized.
Column 4, Line 65, "Streptomyces" needs to be italicized.
Column 4, Line 66, change "tsr" to --tsr--.
Column 5, Line 1, change "cos" to --cos--.
Column 5, Line 25, change "pUC9-tsr" to --pUC9-tsr--.
Column 5, Line 33, change "BClI" to --BclI--.
Column 5, Line 49, change "BClI" to --BclI-- and change "BamHI-cut" to --BamHI-cut--.
Column 5, Line 63, change "Kb" to --kb--.
Column 5, Line 64, change "BamHI" to --BamHI--.
Column 5, Line 67, change "tsr" to --tsr--.
Column 6, Line 9, "Streptomyces" needs to be italicized.
Column 6, Line 32, change "SmaI" to --SmaI--.
Column 6, Line 36, change "SmaI-cut" to --SmaI-cut--.
Column 6, Line 41, "Streptomyces" needs to be italicized, and change "supra," to --supra,--.
Column 6, Line 57, change "BClI" to BclI--.
Column 6, Line 60, change "SmaI" to --SmaI--.
Column 6, Line 65, change "HindIII-EcoRI" to --HindIII-EcoRI--.
Column 6, Line 66, change "HindIII-EcoRI" to --HindIII-EcoRI--.
Column 6, Line 67, change "HindIII" to --HindIII-- and change "EcoRIcut" to --EcoRI-cut--.
Column 7, Line 2, change "HindIII" to --HindIII--.
Column 7, Line 8, change "EcoRI" to --EcoRI--.
Column 7, Line 11, change "EcoRI" to --EcoRI--.
Column 7, Line 12, change "HindIII" to --HindIII--.
Column 7, Line 34, "Streptomyces" needs to be italicized.

UNITED STATES PATENT AND TRADEMARK OFFICE
CERTIFICATE OF CORRECTION

PATENT NO. : 4,874,748

DATED : October 17, 1989

INVENTOR(S) : L. Katz, et al.

It is certified that error appears in the above-identified patent and that said Letters Patent is hereby corrected as shown below:

Column 8, Line 8, change "(Thio®)transformants" to --(Thio$^R$) transformants--.
Column 8, Line 14, change "Thio®" to --Thio$^R$--.
Column 8, Line 32, change "Sau3A1" to --Sau3A1--.
Column 8, Line 37, change "EcoRI" to --EcoRI--.
Column 8, Line 39, change "BglII" to --BglII--.
Column 8, Line 42, change "HindIII" to --HindIII--.
Column 8, Line 43, change "BglII" to --BglII--.
Column 8, Line 47, "in vitro" needs to be italicized.
Column 8, Lines 48-49, change "Gigapack TM" to --Gigapack$^{TM}$--.
Column 9, Line 1, change "eryA" to --eryA--.
Column 9, Line 19, "Streptomyces" needs to be italicized.
Column 9, Line 34, "Streptomyces" needs to be italicized.
Column 10, Line 11, change "Staphlococcus" to --Staphylococcus--.
Column 13, Line 68, change "SmaI" to --SmaI--.
Column 14, Lines 1-2, "Streptomyces" needs to be italicized.
Column 14, Line 3, change "BamHI" to --BamHI-- and change "KpnI" to --KpnI--.
Column 14, Line 6, "Streptomyces" needs to be italicized.
Column 14, Line 9, change "Kb BClI" to --kb BclI--.
Column 14, Lines 59-60, "Streptomyces" needs to be italicized.
Column 15, Line 9, "S. violaceoniger" needs to be italicized.
Column 15, Line 22, "Streptomyces" needs to be italicized.
Column 15, Lines 50-51 (Claim 2), change "2norerythromycin" to
    --2-norerythromycin-- and insert --positive-- after "FAB".
Column 15, Line 68 (Claim 3), insert --or a pharmaceutically acceptable salt
    thereof-- after the structure of the chemical compound.

UNITED STATES PATENT AND TRADEMARK OFFICE
CERTIFICATE OF CORRECTION

PATENT NO. : 4,874,748

DATED : October 17, 1989

INVENTOR(S) : L. Katz, et al.

It is certified that error appears in the above-identified patent and that said Letters Patent is hereby corrected as shown below:

Column 16, Line 3 (Claim 4), "m/z of" should not be italicized and should not be superscript.

Signed and Sealed this

Seventeenth Day of December, 1991

Attest:

HARRY F. MANBECK, JR.

*Attesting Officer*  *Commissioner of Patents and Trademarks*